United States Patent [19]

Morrow

[11] 4,167,633
[45] Sep. 11, 1979

[54] PREPARATION OF 2,4,5,6-TETRAAMINOPYRIMIDINE FROM 2,4,6-TRIAMINOPYRIMIDINE

[75] Inventor: Thomas J. Morrow, Dayton, Ohio

[73] Assignee: The United States of America as represented by the Department of Health, Education and Welfare, Washington, D.C.

[21] Appl. No.: 817,377

[22] Filed: Jul. 20, 1977

[51] Int. Cl.$^2$ .......................................... C07D 239/46
[52] U.S. Cl. .................................................. 544/323
[58] Field of Search ................. 260/256.4 N; 544/323

[56] References Cited

U.S. PATENT DOCUMENTS

| 3,111,521 | 11/1963 | Hoefle et al. | 260/256.4 N |
| 3,128,273 | 4/1964 | Pachter et al. | 260/256.4 N |

OTHER PUBLICATIONS

Traube, Berichte, 37:4546 (1904).
Brown, The Chemistry of Heterocyclic Compounds—The Pyrimidines, pp. 146–151, (1962), pub. by Interscience Publishers.

Primary Examiner—Paul M. Coughlan, Jr.
Attorney, Agent, or Firm—John S. Roberts, Jr.

[57] ABSTRACT

An improved process for the production of

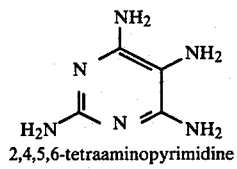
2,4,5,6-tetraaminopyrimidine from

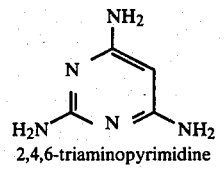
2,4,6-triaminopyrimidine which produces but does not isolate an intermediate

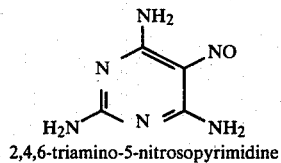
2,4,6-triamino-5-nitrosopyrimidine which compound is retained in situ and minimizes the complex polymer form of a three-dimensional network of azo linkages formed by the nitroso and amino groups. These groups, as they appear in the nitroso intermediate, have carcinogenic possibilities. It has been found that the nitroso compound will precipitate as a stirrable slurry if the temperature parameter is kept low at about 0°–20° C. A preferred route for the production of the nitroso compound from the triamino starting material utilizes as reactants 1.0–1.05 moles of sodium nitrite and 1.5 moles of HOAc in water (HCl may be substituted for HOAc). In the second state of this sequential reaction, the reduction of nitroso is carried out by a reducing agent and one preferred agent is sodium dithionite. Catalytic agents such as Raney nickel and hydrazine or nickel salts, e.g., nickel chloride, and sodium borohydride may also be used. The present process is an improvement in part of the technique of Piper and Montgomery, *J. Het. Chem.*, 11:279 (1974), which process is designed specially to produce the antifolate methotrexate as an end product and is an improvement of the method of application Ser. No. 742,450 of Ellard filed Nov. 17, 1976, entitled "Improved Synthesis of Methotrexate", U.S. Pat. No. 4,080,825.

6 Claims, No Drawings

PREPARATION OF 2,4,5,6-TETRAAMINOPYRIMIDINE FROM 2,4,6-TRIAMINOPYRIMIDINE

This invention relates to the production of

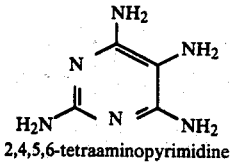

2,4,5,6-tetraaminopyrimidine produced from a starting material

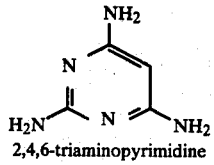

2,4,6-triaminopyrimidine via an intermediate

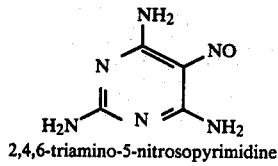

2,4,6-triamino-5-nitrosopyrimidine by an in situ reaction where the intermediate is not segregated. The present procedure is a useful improvement in a portion of the method of producing the antifolate methotrexate by the technique of Piper and Montgomery, J. Het. Chem., 11:279 (1974), application Ser. No. 563,466 of Piper filed Mar. 31, 1975, entitled "Method of Making Pteridine Compounds," U.S. Pat. No. 4,079,056, and of the method of application Ser. No. 742,450 of Ellard filed Nov. 17, 1976, entitled "Improved Synthesis of Methotrexate." The applications above are both incorporated by reference as belonging to a common assignee, the Government of the United States, Department of Health, Education and Welfare (NTIS 242148).

In a preferred procedure in the present invention 2,4,6-triaminopyrimidine is used as a starting material and the intermediate 5-nitroso is prepared by dissolving a ratio of about 1.0 mole of 2,4,6-triaminopyrimidine, 1.0–1.05 moles of sodium nitrite, and 1.5 moles of acetic acid wherein the mix is maintained at about 0°–16° C. or a maximum of 20° C. Hydrochloric acid may be substituted for the acetic acid above. The nitroso compound under these conditions precipitates as a stirrable slurry. The second part of the reaction, i.e., the reduction of the 5-nitroso to 5-amino, is carried out where a reducing agent such as sodium dithionite is added in about 15 minutes to an hour while allowing the reaction temperature to reach 60° C. The product 2,4,5,6-tetraaminopyrimidine is then filtered hot; the filtrate is cooled to 5° C. wherein the product crystallizes and separates with yields of 50–80% and 95% purity as the sulfite. The reduction may also be carried out catalytically as with Raney nickel and hydrazine or nickel salts, e.g., nickel chloride, and sodium borohydride.

It is of importance that about a stoichiometric quantity of nitrite is used with attention to controlling the temperature of the exothermic nitrosation reaction (below 20° C.) followed by reduction when the nitrosation is completed.

Of additional importance, precipitation of the nitrosoamine as a stirrable slurry by conducting the nitrosation at low temperature is essential to the practical success of the method. At higher temperatures the nitroso and amino groups react to form a three-dimensional network of azo linkages which can gel the reaction mixture and even damage the reactor itself.

The starting material 2,4,6-triaminopyrimidine is a known compound and is the subject of a journal article, "The Analysis of 2,4,6-Triaminopyrimidine" which appeared in Manufacturing Chemist and Aerosol News, Nov. 1972, pages 46–53, B. E. Lawrence.

The key literature reference relative to the present reaction and the preparation of 2,4,6-tetraaminopyrimidine is W. Traube, Berichte, 37:4544 (1904). One principal difference and difficulty with using Traube is that the author separates the nitroso derivative with its accompanying difficulties. In the present process the nitroso derivative is not separated but precipitates as a stirrable slurry. This present procedure minimizes the danger of contact with this possibly carcinogenic nitroso derivative. Also, as compared with the preferred present procedure, Traube uses ammonium polysulfide as the reducing agent with the accompanying problems with sulfur and in the first stage uses sulfuric acid, whereas in the present application, either acetic or hydrochloric acid is utilized with nitrite in the production of the nitroso compound. Of these differences, particularly the separation of the 2,4,6-triamino-5-nitrosopyrimidine in Traube is laborious and a 5–6 day filtration is sometimes necessary. Further, this filtration in Traube is accompanied by degradation of the intermediate. The avoidance of this filtration by the present process is deemed of merit.

An incidental disclosure of the product 2,4,5,6-tetraaminopyrimidine is noted as Compound 1B in Baugh and Shaw, J. Org. Chem., 29:3610 (1964).

EXAMPLE 1A

2,4,5,6-Tetraaminopyrimidine Sulfite

A 500-gallon glasslined reactor was charged with 150 gallons of deionized water and 159 pounds of 2,4,6-triaminopyrimidine at 100% as determined by HPLC assay. Glacial acetic acid (13.1 gallons, 114 pounds) was added and the mixture was agitated for 15 minutes to effect solution. The temperature was then lowered to 15° C. through use of brine cooling. At the same time a solution of 88 pounds of sodium nitrite in 35 gallons of water was prepared and charged to another vessel.

The nitrite solution was fed to the 500-gallon reactor over a period of one hour so as not to exceed a batch temperature of 19° C. The first third of the nitrite solution resulted in the batch temperature rise from 13 to 19 despite full brine cooling at 0° C. Upon completion of nitrile addition, the temperature was 12° C. Stirring was continued 25 minutes at 12°–15° C. Heat was applied and addition of sodium dithionite was begun at a batch temperature of 16° C. A total of 384 pounds of dithionite was added over a period of 50 minutes as the temperature was raised to 60° C. The temperature was held at 60°–65° and 4 pounds of activated charcoal and 4 pounds of Celite 545 were added. The batch was filtered hot through a steam heated stainless steel filter into a second reactor followed by addition of 10 gallons of heated water. The filtrate was cooled to 0°–5° With slow agitation and then allowed to stand at 0°–5° for 8 hours. Filtration of precipitated solids gave 144 pounds of 2,4,5,6-tetraaminopyrimidine sulfite based on HPLC assay. This corresponds to a 51% yield based on the triamine charged.

EXAMPLE 1B

In a 500-gallon glasslined reactor, crude damp triaminopyrimidine was dissolved in 150 gallons of deionized water with the aid of 117 pounds of acetic acid. HPLC assay showed 137 pounds of triaminopyrimidine in solution. The solution was cooled to 8° C. and treated with 80 pounds of sodium nitrite in 45 gallons of deionized water over a period of 13 minutes, with full refrigeration on the reactor jacket. A dense granular slurry of nitrosotriaminopyrimidine formed during the next 15 minutes as the temperature rose to 13° C. Analysis showed less than 0.1% of the triaminopyrimidine remaining unreacted in the filtrate, and a sample of the slurry was taken for small scale experiments. It remained a stable slurry under refrigeration for several days. The remainder of the slurry was reduced in situ to tetraaminopyrimidine sulfite by reaction with 382 pounds of sodium dithionite, filtered hot and chilled to 0°–5° C. to precipitate 609 pounds of damp cake, containing 186 pounds of tetraaminopyrimidine sulfite.

EXAMPLE 2

2,4,6-triamino-5-nitrosopyrimidine was prepared by dissolving 1.0 mole of 2,4,6-triaminopyrimidine in 1040 ml of water and 1.5 moles of acetic acid, maintaining the temperature in the range of about 0°–16° C. Then 1.0 mole of sodium nitrite was added to the reaction mixture while controlling the reaction temperature in the range of 0°–20° C.

To the final reaction mixture prepared above, sodium dithionite was added over a period of about 30 minutes to an hour while allowing the reaction mixture to reach 60° C. The reaction mixture was then filtered hot and the filtrate was cooled to 5° C. at which temperature the desired product crystallized from the filtrate and was separated, giving about a 60–75% yield of 2,4,5,6-tetraaminopyrimidine sulfite, which assayed about 95% pure by high pressure liquid chromatography.

EXAMPLE 3

Catalytic Hydrogenation

A 100 ml portion of the nitrosotriamine slurry from Example 1B was treated with 1 gram of Raney nickel and then dropwise with 40 ml of 85% hydrazine hydrate at 16° C. to 50° C. over a period of 70 minutes. The pH was adjusted to neutral by addition of HCl. From time to time from Raney nickel catalyst totaling 1–2 grams was added during two additional hours at 50°. The Raney nickel was removed by hot filtration. The filtrate was adjusted to pH 5.5 and chilled to precipitate 4.4 g of tetraaminopyrimidine monohydrochloride, mp 271.5°–274°, identical by HPLC and stopped flow UV spectroscopy to tetraaminopyrimidine sulfite except for the anion and the difference in molecular weight. Rather than precipitating the tetraaminopyrimidine monohydrochloride, the solution after hot filtration can be used in the Ellard process referred to hereinabove.

I claim:

1. A process of preparing

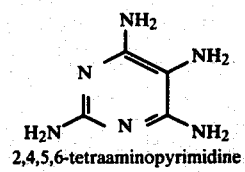
2,4,5,6-tetraaminopyrimidine from

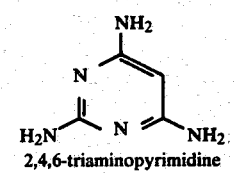
2,4,6-triaminopyrimidine which comprises forming a nitroso intermediate

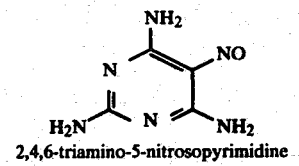
2,4,6-triamino-5-nitrosopyrimidine in situ at low temperatures of about 0°–20° C. in the presence of NaNO₂, HOAc and water to produce a stirrable slurry, and subsequently without separating and in a sequential reaction reducing the 5-nitroso group to 5-amino by means of a reducing agent and filtering to give a solution of 2,4,5,6-tetraaminopyrimidine.

2. The process according to claim 1 wherein the reducing agent is sodium dithionite.

3. The process according to claim 1 wherein the reducing agent is catalytic and is selected from one pair of catalytic reducing agents, namely (1) hydrazine and Raney nickel and (2) nickel salt and sodium borohydride.

4. The process according to claim 1 wherein 2,4,6-triaminopyrimidine is reacted with an equimolar amount of sodium nitrite in the presence of about 1.5 molar amount of HOAc in the presence of water to produce the intermediate 2,4,6-triamino-5-nitrosopyrimidine in the form of a stirrable slurry.

5. The process according to claim 1 wherein about 1 mole of 2,4,6-triaminopyrimidine is reacted with 1.0–1.05 moles of sodium nitrite in about 1.5 moles of HOAc and water.

6. The process according to claim 1 wherein the solution is cooled to precipitate and recover the product 2,4,5,6-tetraaminopyrimidine.

* * * * *